US 7,956,236 B2

(12) United States Patent
Ponomarenko et al.

(10) Patent No.: US 7,956,236 B2
(45) Date of Patent: Jun. 7, 2011

(54) ABSORBENT ARTICLE WITH SUBLAYER

(75) Inventors: Ekatarina Anatolyevna Ponomarenko, Bad Soden (DE); Monika Imgard Johanning, Steinbach/Ts (DE); Ralf Geilich, Eppstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 114 days.

(21) Appl. No.: 11/525,606

(22) Filed: Sep. 22, 2006

(65) Prior Publication Data

US 2007/0073254 A1 Mar. 29, 2007

(30) Foreign Application Priority Data

Sep. 23, 2005 (EP) .................................. 05108793

(51) Int. Cl.
*A61F 13/15* (2006.01)
(52) U.S. Cl. ........ 604/378; 604/381; 604/382; 604/383; 604/385.101
(58) Field of Classification Search .................. 604/378, 604/381–383, 385.101
See application file for complete search history.

(56) References Cited

U.S. PATENT DOCUMENTS

| | | | |
|---|---|---|---|
| 3,860,003 A | 1/1975 | Buell | |
| 4,276,338 A * | 6/1981 | Ludwa et al. | 428/137 |
| 4,610,678 A | 9/1986 | Weisman et al. | |
| 4,834,735 A | 5/1989 | Alemany et al. | |
| 4,895,749 A * | 1/1990 | Rose | 428/132 |
| 4,940,464 A | 7/1990 | Van Gompel et al. | |
| 5,092,861 A | 3/1992 | Nomura et al. | |
| 5,151,092 A | 9/1992 | Buell et al. | |
| 5,246,433 A | 9/1993 | Hasse et al. | |
| 5,260,345 A | 11/1993 | DesMarais et al. | |
| 5,342,338 A | 8/1994 | Roe | |
| 5,368,909 A * | 11/1994 | Langdon et al. | 428/137 |
| 5,387,207 A | 2/1995 | Dyer et al. | |
| 5,397,316 A | 3/1995 | LaVon et al. | |
| 5,478,335 A * | 12/1995 | Colbert | 604/383 |
| 5,509,914 A | 4/1996 | Osborn | |
| 5,533,991 A | 7/1996 | Kirby et al. | |
| 5,554,145 A | 9/1996 | Roe et al. | |
| 5,569,234 A | 10/1996 | Buell et al. | |
| 5,603,707 A | 2/1997 | Trombetta et al. | |
| 5,625,222 A | 4/1997 | Yoneda et al. | |

(Continued)

FOREIGN PATENT DOCUMENTS

EP 0 203 823 A2 12/1986

(Continued)

OTHER PUBLICATIONS

Definitions of feces and excretion, Merriam-Webster OnLine.*

(Continued)

*Primary Examiner* — Jacqueline F Stephens
(74) *Attorney, Agent, or Firm* — John G. Powell; Katheleen Y. Carter

(57) ABSTRACT

An absorbent article including a backsheet, an absorbent core, a topsheet with apertures, and a sublayer that includes at least one acquisition layer. The sublayer includes a multitude of holes. At least some of the apertures overlap partially at least some of the holes to form combined apertures in an overlap area that has an open area of between 15% and 50%. The absorbent article may provide improved isolation of feces away from the skin of a wearer of the absorbent article and/or improved immobilization of feces received by the absorbent article.

7 Claims, 4 Drawing Sheets

U.S. PATENT DOCUMENTS

| | | |
|---|---|---|
| 5,628,097 A | 5/1997 | Benson et al. |
| 5,635,275 A * | 6/1997 | Biagioli et al. ............... 428/132 |
| 5,658,639 A | 8/1997 | Curro et al. |
| 5,718,928 A * | 2/1998 | Rieker ........................ 425/290 |
| 5,885,267 A | 3/1999 | Mishima et al. |
| 5,897,543 A * | 4/1999 | Francis ........................ 604/383 |
| 5,897,545 A | 4/1999 | Kline et al. |
| 5,916,661 A | 6/1999 | Benson et al. |
| 5,957,908 A | 9/1999 | Kline et al. |
| 6,004,306 A | 12/1999 | Robles et al. |
| 6,120,487 A | 9/2000 | Ashton |
| 6,120,489 A | 9/2000 | Johnson et al. |
| 6,423,884 B1 | 7/2002 | Oehmen |
| 6,458,111 B1 | 10/2002 | Onishi et al. |
| 6,528,698 B2 | 3/2003 | Mizutani et al. |
| 6,590,138 B2 * | 7/2003 | Onishi ........................ 604/378 |
| 6,600,085 B2 * | 7/2003 | Sun et al. ..................... 602/56 |
| 6,786,894 B2 | 9/2004 | Divo et al. |
| 6,897,350 B2 | 5/2005 | Yagou et al. |
| 7,005,558 B1 * | 2/2006 | Johansson et al. ............ 604/383 |
| 7,067,711 B2 | 6/2006 | Kuroda et al. |
| 7,132,585 B2 * | 11/2006 | Kudo et al. .................... 604/380 |
| 2003/0045851 A1 | 3/2003 | Vartiainen |
| 2003/0093048 A1 | 5/2003 | McBride |
| 2003/0139719 A1 | 7/2003 | Nanaumi et al. |
| 2003/0187417 A1 | 10/2003 | Kudo et al. |
| 2003/0233082 A1 | 12/2003 | Kline et al. |
| 2004/0087927 A1 * | 5/2004 | Suzuki ........................ 604/378 |
| 2004/0167486 A1 | 8/2004 | Busam et al. |
| 2005/0234410 A1 | 10/2005 | Ashton et al. |
| 2005/0256475 A1 | 11/2005 | Komatsu et al. |
| 2006/0122569 A1 * | 6/2006 | Drevik et al. ................. 604/360 |

FOREIGN PATENT DOCUMENTS

| | | |
|---|---|---|
| EP | 0 953 324 A1 | 11/1999 |
| EP | 1 201 212 A2 | 5/2002 |
| WO | WO 90/14813 A1 | 12/1990 |

OTHER PUBLICATIONS

International Search Report.

* cited by examiner

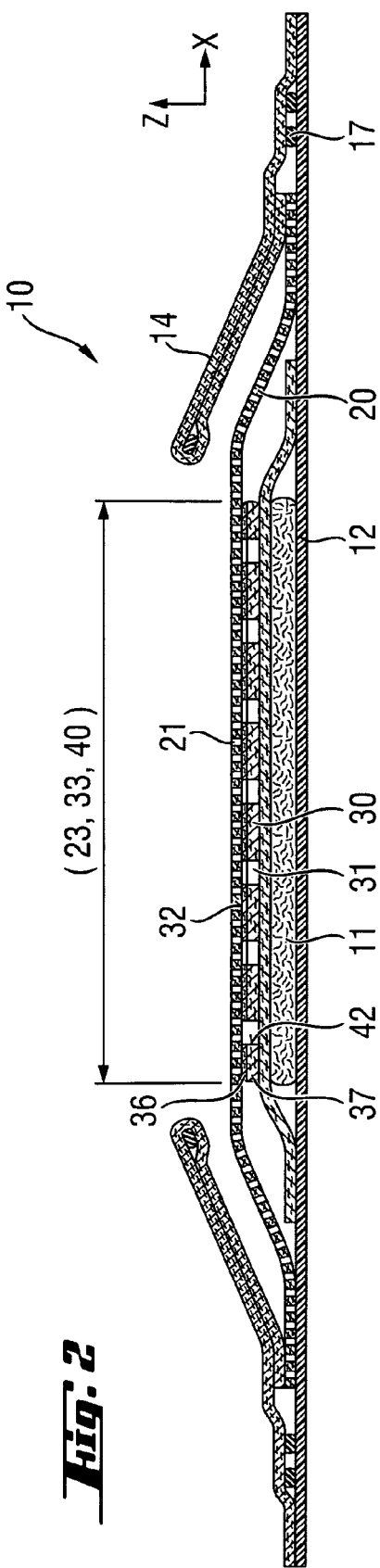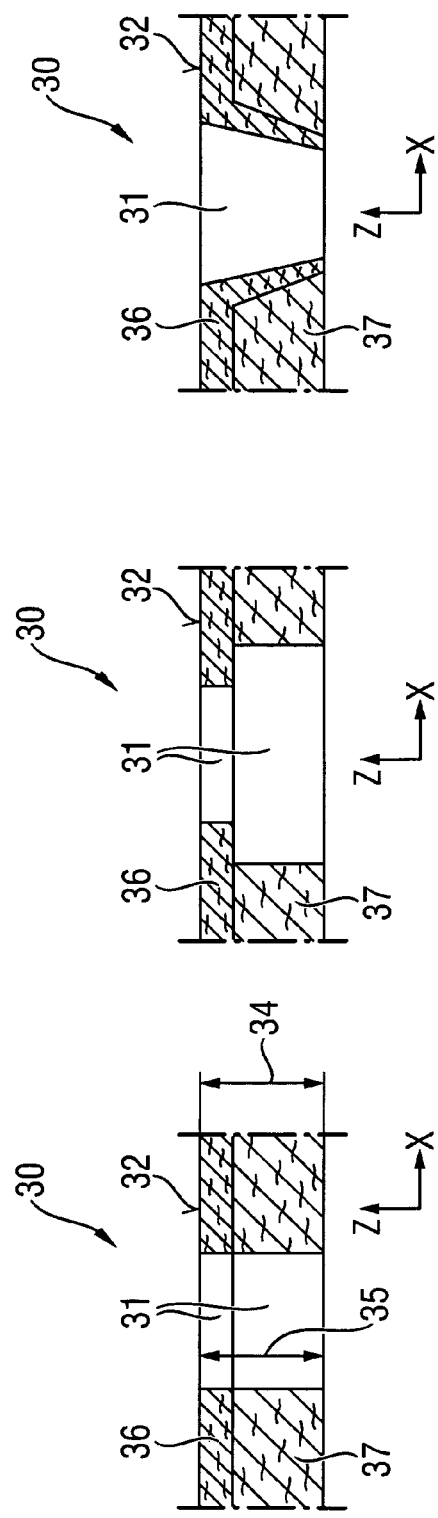

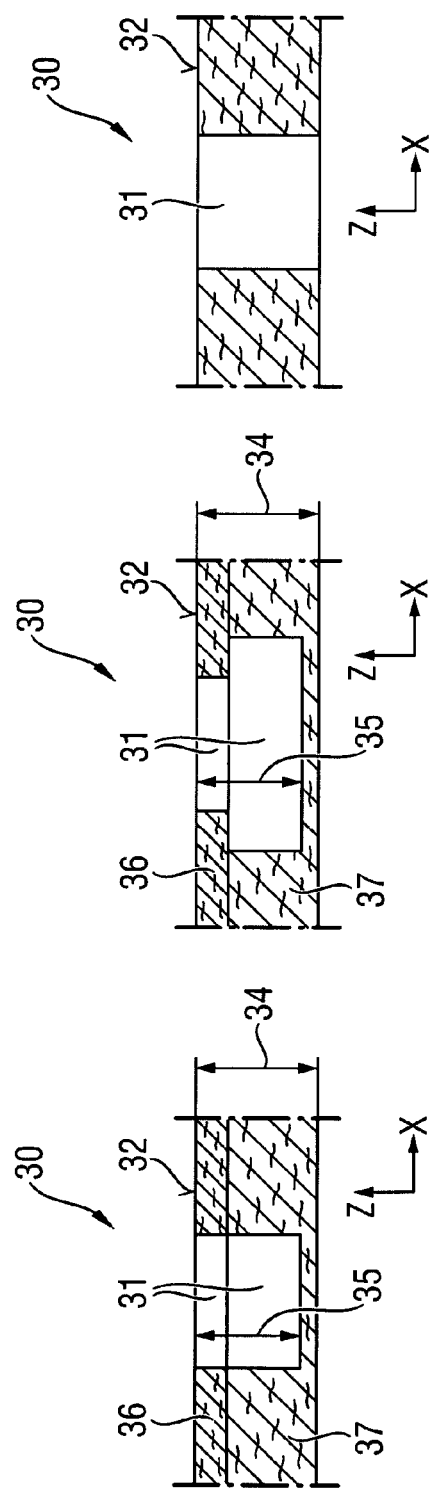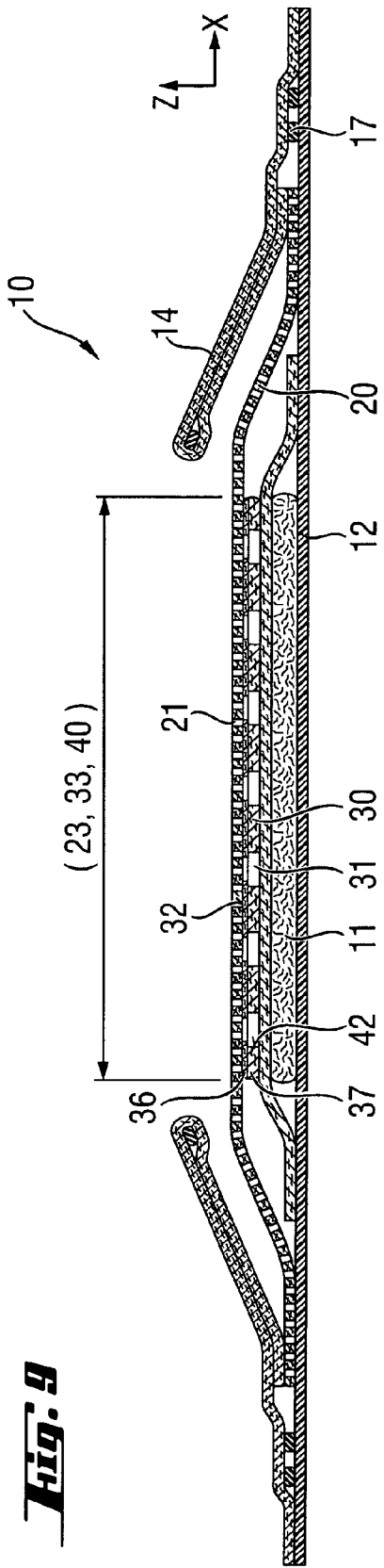

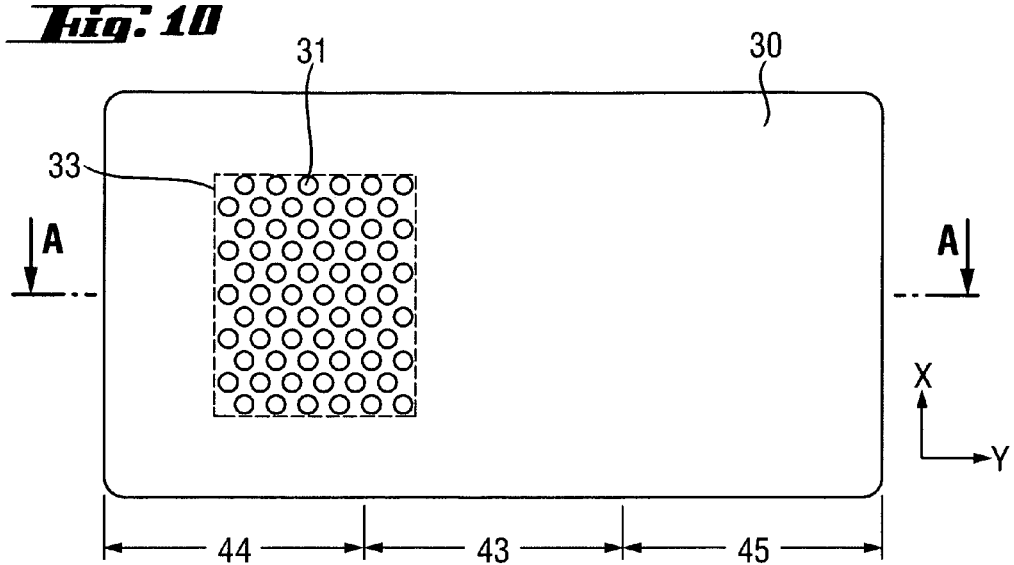
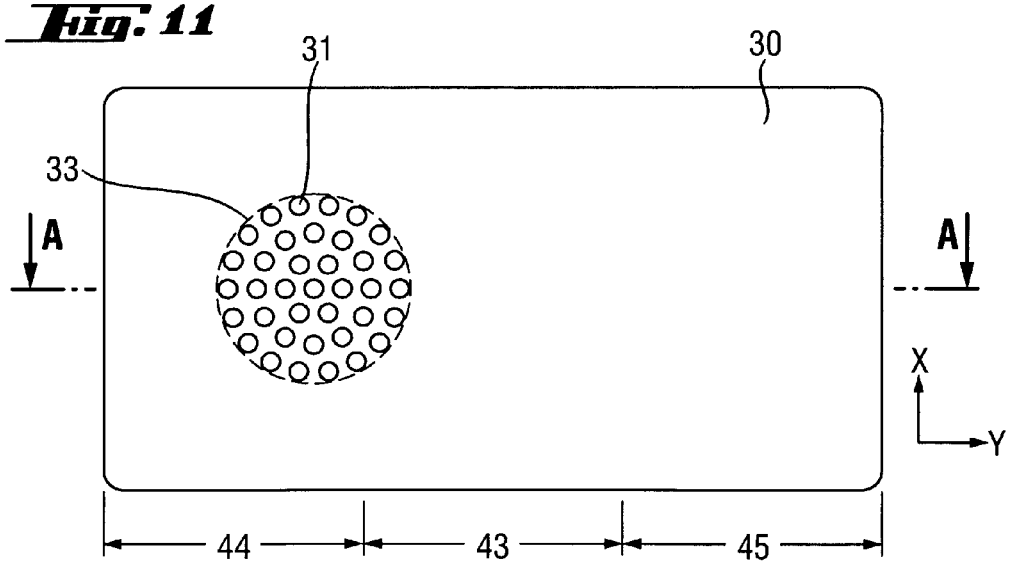
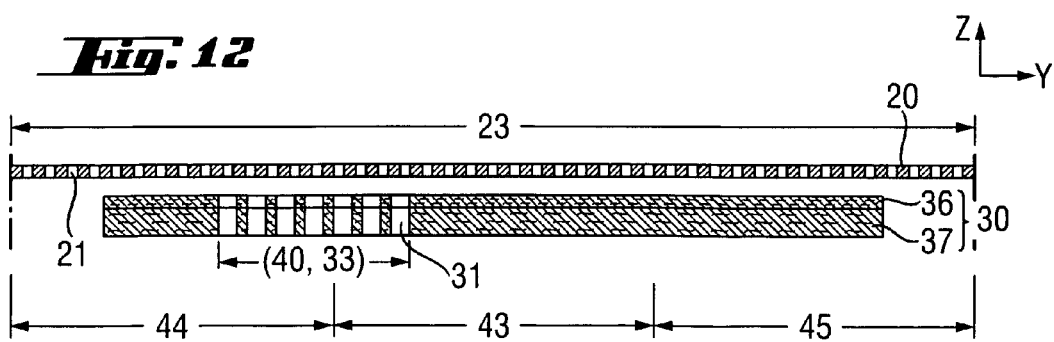

ABSORBENT ARTICLE WITH SUBLAYER

FIELD OF THE INVENTION

An absorbent article having a backsheet, an absorbent core and a topsheet with apertures and including also a sublayer with a multitude of holes whereby at least some of the apertures overlap partially at least some of the holes, resulting in an improved isolation of feces away from the skin and at the same time a reduction of re-soiling of the skin with the isolated feces.

BACKGROUND OF THE INVENTION

It is well known that fecal material is often difficult to remove from the skin of the user, in particular on sensitive skin such as by young babies and the skin around the genitals. Moreover, it is well known that fecal material on the skin can cause irritation and redness of the skin and some times even dermatitis of the skin.

One of the solutions to reduce the fecal material on the skin is to provide a means to isolate the fecal material immediately after discharge, away from the skin. The problem with feces isolation or in diapers is that the feces can vary hugely in consistency and viscosity and furthermore that, whilst isolating the feces, the diaper needs to retain its urine absorption capacity.

Hereto, diapers have been provided with a topsheet with one or more large openings, through which the feces can pass to a void space between the topsheet and the absorbent core. The fecal material is then stored underneath this topsheet, away from the skin.

As alternative, a diaper with a first topsheet with a multitude of small openings has been proposed, allowing low viscosity feces to pass through said openings onto the absorbent core, such that it may be isolated underneath said topsheet and such that the absorbent core may dewater the feces, such as for example taught in U.S. Pat. No. 5,342,338. Optionally, a second topsheet with openings may be present, which further allows immobilization of the feces and dewatering of the feces by the absorbent core underneath.

It has been found that improved feces isolation and immobilization and reduced re-soiling of the skin by the immobilized feces is achieved when the diaper comprises a topsheet with apertures of a specific size and a sublayer with holes of a specific size, which are positioned such that only a small degree of overlap between the holes and the apertures is present. The degree of overlap should be large enough to allow effective passage of feces through the apertures of the topsheet into the holes of the sublayer, but small enough to stop the feces in the holes of the sublayer from migrating back to the skin.

Furthermore, it has been found that the selection of the exact size (dimension) of the holes of the sublayer, at least in the plane of the surface facing the topsheet, are important to achieve effective isolation and immobilization of feces of varying viscosity (including dewatering thereof and storage thereof).

Thus, improved feces isolation, reduced rewet and improved feces immobilization are achieved with the diapers of the invention comprising the specific topsheet and sublayer described herein which have a small percentage overlap between the apertures of the topsheet and the holes of the sublayer.

Furthermore, it has been found that it is beneficial to provide a sublayer that is or comprises one or more acquisition layers that are furthermore pressure resistant even after wetting, to ensure the feces remains immobilized even after the sublayer has been wetted by liquid exudates and submitted to pressure.

BRIEF DESCRIPTION OF THE DRAWINGS

FIG. 2 shows a cross-section view of the diaper (10) of FIG. 1 through the x-direction centre line thereof.

FIG. 3 shows a cross section through a hole (31) of, and surrounding parts of a preferred sublayer (30) of the diaper (10) of the invention as also shown in FIGS. 1 and 2.

FIG. 4 shows a cross section through a hole (31) of, and surrounding parts of another preferred sublayer (30) herein.

FIG. 5 shows a cross section through a hole (31) of, and surrounding parts of another preferred sublayer (30) herein.

FIG. 6 shows a cross section through a hole (31) of, and surrounding parts of yet another preferred sublayer (31) herein.

FIG. 7 shows a cross section through a hole (31) of, and surrounding parts of yet another preferred sublayer (30) herein.

FIG. 8 shows a cross section through a hole (31) of, and surrounding parts of yet another preferred sublayer (30) herein.

FIG. 9 shows a cross section through a preferred diaper (10) herein taken along the x-direction centre line of the diaper, having a sublayer (30) with holes (31) as shown in FIG. 4.

FIG. 10 shows a plan top view of a preferred sublayer (30) for use herein having a rectangular region (33) with holes with a circular circumference in the surface (32) facing the topsheet (20) in the back region (44) and partial crotch region (43) thereof.

FIG. 11 shows a plan top view of another preferred sublayer (30) for use herein having a circular region (33) with holes with a circular circumference in the surface (32) facing the topsheet (20) in the back region (44) and partial crotch region (43) thereof.

FIG. 12 shows a cross section view of the sublayer (30) and topsheet (20), taken along the y-direction centre line thereof, forming an overlap zone (40), said sublayer (30) being for example as shown in FIGS. 10 and 11.

DETAILED DESCRIPTION OF THE INVENTION

Figure 1:
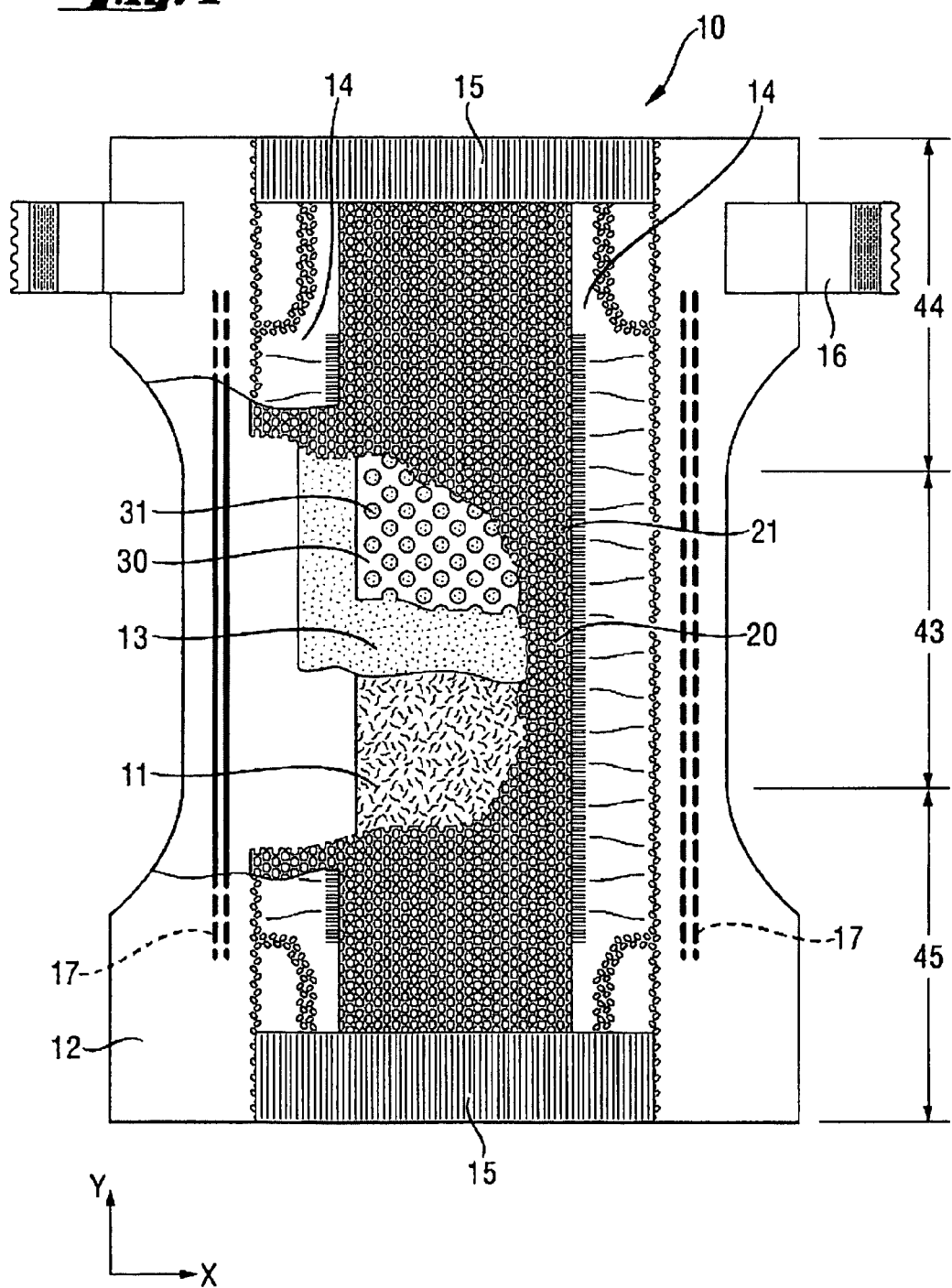
FIG. 1 is a plan top view of a preferred diaper (10) of the invention, with cut out portions to show the sublayer (30) as described herein.

Whilst the invention has been derived while investigating improved feces isolation and immobilization, the sublayer (30) and topsheet (20) with the overlapping zone as described herein may also be used in articles other than those intended for feces handling, for example in sanitary napkins or even panty-liners When used herein, "diaper" means any article intended for use by a baby or infant for collection of feces and/or urine, including, amongst others, also training pants. "Adult incontinence garment", when used herein, includes any article intended for adults for collection of feces and/or urine.

The article (10), topsheet (20) and sublayer (30) herein have a length in longitudinal or y-direction (or Machine Direction), a width in transverse or x-direction (or Cross Machine Direction) and a thickness or caliper in z-direction, as shown in the Figures.

The article (10) and optionally components thereof has a back region (44), crotch region (43) and front region (45), that in use are positioned towards the back, in the crotch, or towards the front of the user, respectively. They typically represent herein each ⅓ of the length of the article.

The surface area of the aperture (21) and hole (31) is the surface area of the cross-section of the aperture (21) or hole (31) in the plane of the body-facing surface of the topsheet (20) and the topsheet-facing surface (32) of the sublayer (30), respectively. The average minimum and maximum dimensions of the apertures and holes and combined apertures are also determined in the cross-section of the aperture (21) or hole (31) in the plane of the body-facing surface of the topsheet (20) and the topsheet-facing surface (32) of the sublayer (30), respectively. The surface area of the combined aperture (42) is the surface area of the cross-section of said combined aperture (42) in the body-facing surface of the topsheet, and similarly, the combined aperture dimensions are determined in said cross section.

FIG. 1 is a plan view of a preferred diaper (10) according to the present invention. The diaper is shown in its flat out, uncontracted state (i.e., without elastic induced contraction). Portions of the structure are cut away to more clearly show the underlying structure of the diaper (10). The portion of the diaper (10) that contacts a wearer is facing the viewer.

The diaper (10) comprises a topsheet (20), as described hereinafter in detail, a backsheet (12), and typically an absorbent core (11), and optionally a core wrapping material (13), and a sublayer (30), as described herein after in detail. Further optional features may be present, such elasticized leg cuffs or elastics (17), barrier cuffs (14), elastic waist feature(s) (15). One end portion of the diaper (10) is configured as a first or front (waist) region (45) of the diaper (10). The opposite end portion is configured as a second, back (waist) region (44) of the diaper (10). An intermediate portion of the diaper (10) is configured as a crotch region (43), which extends longitudinally between the first and second waist regions (44, 45). The crotch region (43) is that portion of the diaper (10) which, when the diaper (10) is worn, is generally positioned between the wearer's legs. The diaper (10) is depicted with its longitudinal axis (Y) and its transverse axis (X). The diaper may also comprise a fastening system, which may include at least one fastening member (16) and at least one landing zone (not shown). Preferred diaper configurations are described generally in U.S. Pat. Nos. 4,940,464, 5,554,145; 5,569,234; 6,004, 306, U.S. patent application Ser. No. 10/171,249 and in U.S. patent application Ser. No. 10/824,121.

The absorbent core (11) in FIG. 1 is disposed between the sublayer (30) and the backsheet (12). The absorbent core (11) may comprise any absorbent material that is generally compressible, conformable, non-irritating to the wearer's skin, and capable of absorbing and retaining liquids such as urine. Exemplary absorbent core structures (11) for use as the absorbent articles (10) herein are for example described in U.S. Pat. Nos. 4,610,678; 4,834,735; 5,260,345; 5,387,207; 5,397,316; and 5,625,222. Preferably, the absorbent core (11) comprises at least a super absorbent material, preferably a superabsorbent polymer material, also referred to as SAP or AGM, that is capable of absorbing at least about 5 times, preferably at least 10 times, its weight of an aqueous fluid such as 0.9% saline as measured using the Centrifuge Retention Capacity test, well known in the art.

The absorbent material in the absorbent core (11) may have a "profiled" distribution, whereby the absorbent core comprises more absorbent material in one area (e.g. the p-point or crotch and optionally front region) than in another area (e.g. back region).

The absorbent core (11) may also comprise a structuring agent or matrix agent, such as absorbent fibrous material, such as airfelt fibers, and/or adhesive, which each may serve to immobilize the water-swellable material.

However, it may be preferred that a relatively low amount or no absorbent fibrous (cellulose) material is used in the absorbent core (11). Thus, it may be preferred that said core (11) herein comprises large amounts of the water-swellable material and only very little or no absorbent (cellulose) fibers, preferably less than 20% by weight of the water-swellable material, or even less than 10% by weight of the water-swellable material, or even less than 5% by weight.

Preferred absorbent cores (11) herein comprise an adhesive or thermoplastic material or preferably a (fibrous) thermoplastic adhesive material, which is laid down onto a layer of water-absorbing and/or -swellable material. Thereby, the thermoplastic or adhesive material provides cavities to hold the water-swellable material and thereby immobilizes this material. Also, the thermoplastic or adhesive material bonds to the substrate and thus affixes the water-swellable material to the substrate. It may be preferred that no absorbent fibrous material is present in the absorbent core (11).

A particularly preferred absorbent core (11) for liquid (e.g. urine) storage is described in U.S. patent application Ser. No. 10/776,839.

The backsheet (12) is preferably joined to the topsheet (20), and optionally the sublayer (30) at least about a portion of the periphery thereof. The backsheet (12) is preferably manufactured from at least a (thin) polymer film. In one preferred embodiment the film comprising backsheet (12) is impervious to liquids. Typically, the backsheet (12) comprises a layer of polyethylene film having a basis weight between about 10 g/m² and about 30 g/m², although other flexible, liquid impervious materials can be used. Preferably, the film is breathable (e.g. via micropores) so as to permit vapors to escape from the diaper (10) while still preventing exudates from passing through the backsheet (12). Particularly preferred backsheet materials have a nonwoven laminated to the film layer so as to make backsheet (12) more "cloth-like". Such a nonwoven layer may comprise a nonwoven material (e.g. one having a spunbonded or other suitable structure) with a basis weight between about 15 g/m² and about 25 g/m². Suitable materials for use as backsheet (12) are available form Clopay Plastic Products Company of Mason, Ohio.

The diaper (10) may also include such other features (not shown) as are known in the art including front and rear ear panels, waist cap features, elastics, topsheet (20)s with aperture(s) and elastics, and the like to provide better fit, containment and aesthetic characteristics. Such additional features are well known in the art and are e.g., described in U.S. Pat. No. 3,860,003 and U.S. Pat. No. 5,151,092 and EP1201212-A.

The preferred absorbent articles herein are refastenable diapers (10) (diapers with fasteners) and pant-type diapers, i.e. training pants. Suitable pant-type diapers are disclosed in U.S. Pat. Nos. 5,246,433; 5,569,234; 6,120,487; 6,120,489; 4,940,464; 5,092,861; 5,897,545; 5,957,908 and in Published U.S. Pat. Application 2003/0233082A1.

Topsheet (20)

The topsheet (20) of the articles (10) of the invention comprises apertures (21) that are through-apertures (21), i.e. where the apertures (21) are through the whole thickness (z-direction) of the topsheet (20).

The topsheet (20) may be embossed, but in a preferred embodiment, the topsheet (20) is flat and the average caliper of the topsheet (20) equals the average caliper or depth of the apertures (21), as shown in FIG. 2.

The apertures (21) of the topsheet (20) are small, having an average greatest dimension (in the plane of the topsheet (20)) of from 2 to 8 mm, preferably from about 2 mm to 6 mm, or even more preferably from 2.4 to 6 mm, or even more preferably from 3 to 5 mm or to 4 mm.

Preferably, the apertures (21) have also an average smallest dimension of from 2 mm to 6 mm, and preferably from 3 to 5 mm.

The average aperture dimension is determined in the cross section of the apertures on the surface of the topsheet (20) that faces the body of the wearer when in use and can be determined by the method set out herein below.

Preferably, the apertures (21) are such that the greatest dimension is through the centre point of the aperture (21). Preferably, the apertures (21) have an oval and/or circular circumference, as shown in FIGS. 1 and 2.

The average shortest (smallest) distance between the middle points of neighboring apertures (21) is preferably from 2 to 7 mm, or more preferred from 4 to 6 mm.

Each region (23) of apertures (21) has an open area, which is the sum of the surface areas of said apertures (21) of said region (23), as measured in the cross section of the apertures (21) in the body facing surface of the topsheet (20). This can be determined by the method described herein below.

This open area of each region (23) is of from 20% to 55% of the total surface area of said region, and preferably from 30% to 50%, or even more preferably from 30% to 45% thereof.

Preferably, the total open area of the topsheet (20) (which is the sum of open area of the regions of the topsheet with apertures (21) of the topsheet (20)) is from 15% to 55%, and preferably from 20% to 50% or even more preferably from 25% or 30% to 45%, of the total surface area of the topsheet (20).

Preferably the topsheet (20) comprises a single region (23) with apertures (21) which is typically about 60% to 100% of the total surface area of the topsheet (20), preferably about 80% to 100% of the total surface area of the topsheet (20). Thus, in a preferred execution, the whole topsheet (20) comprises said apertures (21) and thus, there is only one region with apertures (21) in the topsheet (20) that is 100% of the topsheet (20) surface area, as is shown in FIGS. 1 and 2.

In another preferred execution, the topsheet (20) has one region (23) with apertures (21) that is centered in the topsheet (20), such that said region (23) is not present along the longitudinal and transverse edges of the topsheet (20), i.e. so that no apertures (21) are present along said edges.

The topsheet (20) can be made of liquid permeable or impermeable material, because due to the apertures (21), the urine and feces will pass easily and quickly to the sublayer (30) and the absorbent core below. The topsheet (20) may be (made of) a nonwoven or woven web with apertures (21) that is made of synthetic and/or natural fibers, or it may be an apertured or apertured formed polymer film, or a combination thereof, as known in the art and for example described in U.S. Pat. No. 5,342,338 and EP-A-0203823.

Preferred apertured topsheets include fibrous nonwoven webs, made of polyolefin, preferably of polyethylene, polypropylene or copolymers thereof, or mixtures thereof.

Preferred topsheets (20) herein are made by forming apertures (21) in a continuous uninterrupted film or web of a thermoplastic polymer, for example polyolefins, and/or by providing a film or web with a plurality of spaced apart discrete bonds and weakening the web or film at a plurality of locations whereby a portion of the spaced part bonds are separated from said weakened locations, and subsequently applying a tensioning force to said web or film to rupture the weakened locations, e.g. by stretching said film or web, to form thus apertures.

Preferred processes for making apertured films or webs as used herein are described in U.S. Pat. No. 5,916,661, U.S. Pat. No. 5,658,639 and U.S. Pat. No. 5,628,097.

The nonwoven webs with apertures (21) useful herein as topsheet (20) comprise preferably polyethylene and/or polypropylene and/or polyester fibers and preferably have a basis weight of about 15 to 30 $g/m^2$ or to 25 $g/m^2$. Preferred are carded nonwoven webs, including carded hydro-entangled and carded through-air bonded nonwoven webs.

The topsheet (20) is typically non-liquid retaining in use, to ensure the liquid (e.g. urine) is transported immediately through the topsheet (20) (the apertures (21) thereof and optionally through the topsheet (20) material itself) to the underlying acquisition sublayer (30) and absorbent core (11).

The topsheet (20) may comprise a skin care lotion as known in the art. It may be preferred that this is applied in the form of stripes on the topsheet (20), preferably in the form of longitudinal (Machine Direction) stripes.

The topsheet (20) may be completely or partially attached to the sublayer (30) described herein after. This may be done by any known method in the art, preferred methods include adhesive bonding. It may be preferred that the topsheet (20) and sublayer (30) are only partially attached to one another, for example 50% to 80% of the corresponding surface area between the topsheet and sublayer.

Unlike the sublayer (30) described below in more detail, the topsheet (20) is thin, e.g. less than 1.0 mm or typically even less than 0.5 mm thick, and may be hydrophilic or hydrophobic, because it merely serves to pass the liquid and feces directly through to the sublayer (30) below, and will typically not contain the liquid or distribute the liquid in x and y direction.

Sublayer (30)

The sublayer (30) typically comprises fibers or is fibrous, and said fibers may be non-bonded or bonded with a binder. Also, the sublayer (30) herein comprises or is typically one or more acquisition layers (e.g., that can temporarily absorb fluids, like urine, and pass on or transport the fluid to the absorbent core that is in proximity to said sublayer (30)). Furthermore, the sublayer (30) is typically compression resistant even after wetting, retaining a minimum caliper after wetting and under compression compared to the sublayer (30) in dry state (prior to wetting) under the same compression. This ensures an excellent feces storage and isolation and during the whole usage of the diaper, even when a user is moving or sitting on the diaper. Highly preferred may be that the sublayer (30) comprises two or more (acquisition) layers (e.g., a laminate of two or more layers), and that the holes (31) of the sublayer (30) are preferably formed by the (aligned) holes (31) through either the first or second or first and (part of the) second or subsequent layers. Preferably, the first layer (36), in use facing the topsheet (20), has holes (31) that have a smaller average surface area (as measured on the surface of the first layer (36) that faces the topsheet (20) than the holes (31) of the second layer (37), as measured on the surface of the second layer (37) that faces the first layer (36). The first and second acquisition layers (36,37) are then thus both layers or sheets that have their maximum dimensions in x- and y direction and that are parallel to one another. In one embodiment, the first and second layer are placed onto one another, but in another embodiment a further (acquisition) layer may be present between the two acquisition layers (36,37). The sublayer (30) may be obtained by forming holes (31) into a sublayer (30) material by any known hole-forming method, either prior to incorporating it into the diaper, or once incorporated in the diaper, or the sublayer (30) can be formed directly with holes (31) (e.g., by laying material of the sublayer (30) or one of the layers thereof, such as fibers, around shaper portions or protrusions of a forming surface, so that the protrusions or shaped portions shape the holes (31), as described herein).

In general, the sublayer (30) herein is (serves as) an acquisition layer and optionally also (as) a distribution layer, capable to acquire liquid (urine) and temporarily hold the liquid and allow it to pass, or transport it to the absorbent core underneath (in Z-direction), and optionally also distribute it in the X and Y direction of the sublayer (30). It typically does not serve to hold or store fluid (urine) for a longer period or permanently, but it facilitates the absorption of the fluid by the absorbent core below. However, the sublayer of the article (10) of the invention does serve to store and/or immobilize fecal material in the holes (31) of the sublayer (30).

The sublayer (30) herein is thereto typically hydrophilic and it typically does not comprise any super-absorbent materials, or water-swelling materials, such as generally referred to as SAP and AGM particles, further described herein above.

The sublayer (30) comprises typically a fibrous layer, and it comprises preferably two layers or more that are fibrous layers. This is further shown in FIGS. 2 to 7 and 12.

The holes (31) of the sublayer (30) herein are capable to store and immobilize feces and they include blind holes (31), as for example shown in FIGS. 6 and 7, and through holes (31), as for example shown in FIGS. 1-5 and 8. When the holes (31) are blind holes (31), it is still preferred that the holes (31) have an average depth or caliper that is about 50% to 95% of the average thickness or caliper of the relevant region of the sublayer (30) with said holes (31), or the average thickness or caliper of the sublayer (30) as a whole. If the sublayer (30) comprises two or more layers, then the sublayer holes (31) referred to herein are preferably through or in two or more layers The holes (31) of the sublayer (30) have an average smallest dimension as defined herein that is larger than the average greatest dimension of the apertures (21) of the topsheet (20).

The holes (31) of the sublayer (30) have typically a larger average surface area than the average surface area of the apertures (21) of the topsheet (20), as described above (although the open area of the sublayer (30) may preferably be less than the open area of the topsheet (20), as is clearly shown in FIG. 12.

The holes (31) of the sublayer (30) have an average smallest dimension of 3 to 10 mm, preferably from 4 mm to 10 mm, or more preferably from 4 mm to 8 mm, or even more preferably from 5 mm to 7 mm, said average being the average over the total of smallest dimensions of the holes (31) in the sublayer (30). This can be determined by the method described herein below.

The circumference of the holes (31) of the sublayer (30) may have any form, including rectangular (so that the holes (31) are in the form of stripes or channels), but preferably the holes (31) are square, oval, or more preferably the sublayer (30) comprises holes (31) with a circular circumference, including thus preferably substantially cylindrical holes (31), as shown in FIGS. 1, 10 and 11.

Preferably, a hole is such that the smallest dimension is through the centre point of said hole.

The average shortest (smallest) distance between neighboring holes (31) (from edge to edge, in the plane of the surface facing the topsheet) is preferably from 2 mm to 10 mm, or more preferably from 3 mm to 7 mm.

The sublayer (30) herein has a region (33) with through or blind holes (31) that has an open area of from 15% to 50% of the total surface are area of said region (33), (whereby the open area is the sum of the surface areas of the holes (31) as measured in the cross section of the holes in or on the surface (32) of the sublayer (30) that faces the topsheet (20)). Preferably the open area of a region (33) with holes (31) of the sublayer (30) is from 25% to 45% or even more preferably from 30% to 40% or to 35% of the total surface area of the region.

The sublayer (30) may comprise one or more regions with holes (31), typically such that the region(s) is (are) at least present in the crotch and/or back region of the sublayer (30), as shown in FIGS. 10 and 11.

In one preferred execution, shown in FIGS. 10 and 11, the sublayer (30) comprises a single region (33) with holes (31), typically in the back region (44) and part of the crotch region (43) of the article, e.g. the back ⅔ or 65% or less of the surface area of the topsheet or diaper (10), preferably the back 60% or even more preferably the back 50% thereof. Thus, preferably, the region or regions form at least 30%, more preferably at least 35% of the total surface area of the sublayer (30), and preferably at the most 65%, or even at the most 60% of said surface area of the sublayer.

Preferred is that the open area of the sublayer as a whole is less than 45%, preferably between 15% and 40%, or more preferably between 20% and 35%.

The sublayer (30) may have the same width and length dimensions as the topsheet (20), but it may be preferred that the sublayer (30) has a smaller width dimension and/or optionally a smaller length dimension than the topsheet (20). FIG. 1 shows such an execution whereby the width of the sublayer (30) is smaller than the width of the topsheet (20). FIG. 12 shows an embodiment whereby the length of the sublayer (30) is smaller than the length of the topsheet (20).

Preferably, the surfaces of the sublayer (30) that face the topsheet and the absorbent core are flat.

When the holes (31) in the sublayer (30) are blind holes (31), then the holes (31) typically have an average caliper or depth that is at least 70%, or preferably at least 80%, or when possible even at least 95% of the average caliper of the sublayer (30) or relevant region (33) thereof.

The sublayer (30) (and the through holes (31) of the sublayer (30)) have preferably an average caliper or depth (34, 35) of at least 2 mm, preferably at least 3 mm, or even at least 4 mm, at least in the regions (33) of the sublayer (30) that comprises said holes. The preferred maximum caliper of the sublayer may be 8 mm or more preferably 6 mm, for wearer's comfort.

The caliper or depth (35) of the holes can be determined by the method set out herein below.

The sublayer (30) and/or the holes (31) of the sublayer (30) have preferably an average caliper or depth (35) of at least 2 mm, preferably at least 3 mm, or even at least 4 mm, at least in the part of the sublayer (30) that forms the overlap zone (40). The caliper or depth (35) of the holes can be determined by the method set out herein below.

The sublayer (30) as a whole may also have the above average caliper (34), but it may be slightly more, e.g. when the holes (31) are blind holes, as described above and shown in FIGS. 6 and 7.

The sublayer (30) that is present in the overlap zone (40) is preferably compression resistant even after wetting, such that its average caliper (34) loss after wetting (wet resilience) is less than 20% or even more preferably less than 15%, or even more preferably less than 12%, or preferably even less than 10%. Average caliper (34) loss after wetting (wet resilience) is determined by the method set out herein below.

As described above, preferred articles (10) herein have at least three layers with apertures (21) or holes (31), namely a topsheet (20) with apertures (21) and a sublayer (30) comprising at least two layers (a first layer (36) and second layer (37) and optionally further layers) with holes (31), whereby the holes (31) of the (at least) two layers of the sublayer (30) form together the holes (31) of the sublayer (30), as for example shown in FIGS. 1, 2 and 12.

The layers (36, 37) of the sublayer (30) may alternatively be such that one comprises said holes, e.g. the second layer (37) may comprise holes and the first layer (36) may be formed into said holes, being thus also present on the sidewalls of said of the holes 931) of the sublayer (30), or the first layer (36) only comprises holes, so that in each case, the holes (31) of the sublayer (30) are blind holes.

Alternatively, two or more of the layers (36, 37) of the sublayer (30) comprise holes that form together the holes (31) of the sublayer (30).

It may be beneficial to have three or more acquisition layers in the sublayer (30), so that the holes are in or through some or all of the three or more acquisition layers, fulfilling the requirements set out herein. Then, the first layer is in contact with the topsheet and with the second layer and typically not in contact with the x-y direction extending-portions of the third and further acquisition layer. The first acquisition layer has typically a width and length than equals or is smaller than the width and length of the further acquisition layers.

The holes through the layers (36, 37) of the sublayer (30) may be fully aligned and overlapping. However, it may be preferred that the holes (31) of the first layer (36) of the sublayer (30), facing the topsheet (20) have a smaller surface area than the holes (31) of the second or further layer there underneath, as shown in FIGS. 4 and 5. In other words, said sublayer (30) may for example comprise a first layer (36), facing the topsheet (20) and a second layer (37), positioned between the absorbent core and said first layer (36), whereby the holes (31) of the sublayer (30) are through the first layer (36) and at least partially through said second layer (37), and whereby the average surface area (in the plane of the topsheet (20)-facing surface of said first layer (36)) of said holes (31) through the first layer (36) is smaller than the average surface area (in the plane of the first-layer face surface of the second layer (37)) of said holes (31) in the second layer (37).

It may be preferred that the first layer (36) is also present on the side walls (in the z-direction) of the holes (31), e.g. the first layer (36) is formed into the holes (31), in particular if the second layer (37) comprises fibers that are non bonded or partially bonded and are thus prohibited from moving into the holes by the first layer (36).

When used herein the surface area of the holes (31) and the open area of the regions (33), determined on the surface of the sublayer (30) facing the topsheet (20) (e.g. of the first layer (36) of the sublayer (30) in the embodiment described above).

The surface area of the overlap zone (40) and the open area of the overlap zones (40), described below, are determined on the surface of the topsheet (20), facing the user in use.

It is preferred, for example, that the sublayer (30) comprise an acquisition layer (e.g. second layer 37)) of unbonded polypropylene (PP) and/or polyester, or preferably polyethylene teraphthalate (PET) fibres.

Also highly preferred may be that the sublayer (30) comprises an acquisition layer (e.g. layer 37) comprising a modified (cellulose) fibers, preferably chemically stiffened, twisted and/or curled (curly) (cellulose) fibres, preferably chemically stiffened, twisted and/or curled crosslinked cellulose or cross-linked synthetic fibres, preferably cellulose fibres. Preferred may be materials available from Weyerhaeuser under as CMC520 and CMC517.

It may also be preferred that the sublayer (30) comprises, in addition to the fibrous acquisition layer above, one or more layers of nonwoven acquisition layers, including carded bonded nonwoven acquisition layers, such as carded resin-bonded nonwovens, embossed carded resin-bonded nonwoven acquisition layers, and optionally highloft carded resin-bonded nonwoven acquisition layers, or preferably carded through-air-bonded nonwoven acquisition layers, carded thermo-bonded nonwoven acquisition layers; most preferably are non-embossed carded resin-bonded non-woven acquisition layers. It is preferred that such materials have a high basis weight, i.e. of 40 gsm or more, preferably even 60 gsm.

Materials that may be used herein are available from BBA Fiberweb/Tenotex (Italy) under the trade name Printex AQL1 Phil (43 gsm, white); or from Freudenberg/Halifax under the code AL 1060 (SC V and SO, and AR10) and under the code114/011/05 (typically 43 or 60 gsm); or from Lohmann, under the trade name Paraprint.

The sublayer (30) may be made by forming holes (31) in a continuous sublayer (30) (i.e. without holes (31)), for example by punching or pushing holes (31) in a said sublayer (30). If the sublayer (30) comprises two or more components or layers, then the holes (31) may be punched or pushed in two or more components or layers, either separately or at the same time.

When the sublayer (30) comprises two or more layers, it may be beneficial that the holes (31) are formed by pushing, e.g. by pushing a hole forming tool onto the surface of the first layer (36) and through the first and second layer (37) and further layers, such that part of the material of the first layer (36) is pushed into the holes (31), to cover (part of) the walls of the holes (31). This may provide smooth edges and walls of the holes (31), and furthermore it may inhibit the fibres of the second layer (37) to migrate into the holes (31). This embodiment whereby the first layer (36) is present on the walls of the holes (31) is shown in FIG. 5.

It may also be preferred to form the holes (31) of the sublayer (30) by laying down the material, e.g. fibres, of the sublayer (30) on a forming surface, around for example protrusions or around shaped portions that hereby shape the holes (31). For example, fibres may be laid down on a forming drum with protrusions in the required hole-pattern of the sublayer (30), around said protrusions to thus shape the holes (31), and the fibres may then optionally be bonded by known bonding techniques.

It may also be preferred that a second (37) and optional further layers with holes are first obtained and subsequently a first layer (36) is placed on top and the first layer is partially pushed into the holes of the second (37) and further layers, to form the sublayer (30) described above.

It may also be preferred that the sublayer (30) comprises one or more layers formed by one of the methods above and one or more layers formed by a different method, as described above. For example, a sublayer (30) may comprise a second layer (37) formed by the lay-down technique above and a first layer (36) formed by punching or pushing, whereby the second holes (31) are punched or pushed either prior to combining the two or more layers, or after combining the two or more layers.

In another embodiment, there may be a caliper (34) gradient of the holes (31) in a region, or between different regions (31), so that for example the holes (31) in one (part of a)

region (31) have a greater caliper than in another region (31) or than in another part of the same region (31).

Overlap Zone(s)

The topsheet (20) overlies the sublayer (30) either partially, or typically completely, as described above, and as shown in FIGS. 1, 2 and 12. This includes the embodiment that the sublayer (30) has a smaller surface area than the topsheet (20), either having a smaller width (cross-machine direction) or length (machine direction) or both, as shown in FIGS. 1, 2 and 12.

At least one region (23) with apertures (21) of the topsheet (20) overlies a region with holes (31) of the sublayer (30), either partially or completely, such that an overlap zone (40) exists, where at least some of the apertures (21) are positioned above at least some of the holes (31), completely and/or partially, to form combined apertures (42).

The combined apertures (42) allow direct passage of feces (and liquids) from the user through the topsheet (20) into the holes (31) of the sublayer (30).

However, the region(s) (33) of the sublayer (30) and the holes (31) thereof, and the region (23) of the topsheet (20) and the apertures (21) thereof, and the overlap zone (40) are created such that the amount of feces that can transfer back to the skin of the user is minimised, whilst still allowing the required passage of the feces to the holes (31) of the sublayer (30) and immobilisation and isolation of the feces in the holes (31) of the sublayer (30).

The overlap zone (40) has an open area (which is the sum of the surface areas of the combined apertures (42) therein in the plane of the body facing surface of the topsheet (20)) of from 15% to 50% of the surface area of said overlap-zone, or preferably 20% to 45% or even more preferably 25% to 35%.

Typically, the total surface area of said overlap zone (40) is at least 2 cm×3 cm (CD×MD) in order to have sufficient surface area to receive the feces and transport it through the apertures (21) into the holes (31). Hereby the width and length dimensions of 2×3 cm are average values. More than one overlap zone (40) may be present and then the total of the overlap zones (40) should be at least 2 cm×3 cm as above, but preferably each overlap zone (40) is at least 2 cm×3 cm as above.

It is preferred that the overlap zone (40) be present in the back and crotch portions of the article (diaper), or part thereof, but not in the front portion of the article (diaper).

In a preferred embodiment, the absorbent article (10) has one single overlap zone (40), and preferably also only one region (33) of holes (31) in the sublayer (30), and the topsheet (20) overlays this region completely, and then this single overlap zone (40) is preferably at least positioned in the crotch (43) and/or back portion (44) of the article, as described above, as shown in FIG. 12, e.g. in the back 70% of the surface area of the article (10) or topsheet (20) thereof.

The overlap zone (40) may have any shape, including circular, oval, rectangular, triangular, or square. Since the region (33) of the sublayer (30) is typically smaller in surface area than the region (23) of the topsheet (20), the shape of the overlap area is typically determined by the shape of the sublayer (30), as shown in FIGS. 10, 11 and 12.

The sublayer (30) (and/or the topsheet (20)) may comprise registrable marks that allow registration of the sublayer (30) and its holes (31) thereof (and/or the topsheet (20) and its apertures (21)) to allow correct alignment and/or partial alignment of the holes (31) of the sublayer (30) and the apertures (21) of the topsheet (20).

Test Methods

Open Area Determination; Aperture and Hole Dimensions and Surface Areas Determination The open area of the regions (23, 33) of the sublayer (30), topsheet (20) and of the overlap zone (40) as used herein can be determined by light microscopy as follows.

Depending on the size of the region (23, 33) or overlap zone (40), said region or overlap zone (40) is each analyzed either as a whole, or in separate portions, to reach an open area value of the whole region (23, 33) or overlap zone (40).

To determine the open area of the overlap zone (40), a sample is prepared by taking the topsheet (20) and the sublayer (30) to be analyzed from the absorbent article, in such a manner that they do not move with respect to one another, in order to keep the overlap zone (40) the same. Alternatively, the sublayer (30) and topsheet (20) are first marked such that after removal from the article, the topsheet (20) can be placed onto the sublayer (30) in its original position, to obtain the same overlap zone (40).

Then, the open area and aperture dimensions of the overlap zone (40) can be determined (by measuring and viewing the surface area that in use faces the user).

To determine the open area and aperture/hole dimensions of the topsheet (20) and sublayer (30), these will have to be separated in the above sample, or new samples of the topsheet (20) and sublayer (30) will have to be made for analyses.

Any sample size can be submitted to the light microscopy, but typically the sample will not be bigger than 15×15 cm. If the region and/or sublayer (30) is or are bigger than this, they may be cut into separate samples by any suitable technique, and each sample can be measured.

The light microscope (JAI CV-M1 E Monochromic Camera; with as lens a Micro-zoom-0.1-0.7) is connected to an interface (ITI-Vision-Itex) that is connected to a computer that runs Optimas software (Media Cybernetics, L.P. Optimas version 6.51) that will do all calculations. Any suitable external light source may be used, for example Kaiser e-Vision.

The sample is placed onto a black cardboard without stretching, without wrinkles or folds. This is placed under the light microscope and the zoom is adjusted to 3.5 and focused until a clear picture is obtained. Then the sample is removed and a ruler is placed under the microscope.

The calibration is then started with the software.

The software will calculate the average smallest and greatest aperture or hole sizes in the cross sections of the apertures and holes on the surface of the sample, and the open areas thereof.

The measurement can be repeated twice to obtain 3 values and an average of the three values.

Caliper (34)

This method uses a (calibrated) Micrometer, under 23° C. and 50% humidity conditions, whereby the Micrometer has an accuracy minimum of 0.01 mm, lowering speed of 3 mm/s, dwelling time of 2-5 sec., such as for example a Frank Type 16303 available from Twing Albert-Frank Gmbh. The Micrometer has a loading 266 grams and an anvil 40 mm in diameter (resulting in 0.3 psi).

The material to be measured is equilibrated for at least 2 hours at 23° C. and 50% humidity prior to the measurement. If the material is to be cut prior to the measurement, the cutting should be done such that the caliper does not change, e.g. without compression in the area that is to be measured. The material should be free of wrinkles, folds, or defects in the area that is to be measured.

The material is placed under the micrometer and the caliper is recorded after the dwelling time.

Five samples can be made and measured to calculate the average caliper.

Average Caliper (34) Loss After Wetting (Wet Resilience).

The following test method determines the wet resilience of the sublayer (30) (that is part of the overlap zone (40)) under a pressure of 0.3 psi, after wetting the sublayer (30), and this is translated in the caliper loss values referred herein.

The sublayer (30) and topsheet (20) are removed from the absorbent article (10). (For measurement purposes, the topsheet (20) is included in this measurement, but the caliper values of the topsheet (20) are deducted, as described below).

In some embodiments, the sublayer (30) may be enclosed between an absorbent core cover (13) and the topsheet (20), in particular when the sublayer (30) is not a web or film, but comprises for example only partially bonded or non-bonded fibers. If such a core cover or core wrap (13) is present, this should be removed from the article together with the sublayer (30) and the topsheet (20), to obtain the sample used herein, containing the core cover (13), sublayer (30) and topsheet (20).

The samples are conditioned for 2 hours at 23° C., 50% humidity and the tests are conducted at the same conditions.

Then, the weight of each sample is determined by any standard method.

First, under a pressure of 0.3 psi, the caliper (34) of the dry sample as a whole and the caliper of the topsheet (20) and optionally the core cover are determined. The caliper (34) under said pressure of the topsheet (20) and optionally the core wrap (13) are deducted from the overall caliper, to obtain the caliper (34) under pressure of the dry sublayer (30). The caliper of the sublayer (30) and topsheet (20), and optionally the core cover (13), are measured in the overlap zone (40), by measuring the caliper thereof in at least 3 points and taking the average thereof (hereinafter referred to as the (average) dry caliper (34) under pressure). The same is done for the caliper under pressure of the topsheet (20) and optionally the core cover (13) (which may be combined into one set of measurements to obtain their combined average caliper under pressure).

Then the dry calipers are measured as set out above, with a Micrometer (e.g. Frank type 16303) with a pressure foot diameter of 40 mm, with a pressure of 0.3 psi, with a lowering speed of 3 mm/s.

Caliper readings are taken 1 minute after the pressure foot is contacted with the surface of the sample.

Then, the sample is loaded with 10 ml saline solution (0.9% NaCl in de-mineralized water) per gram sample, by gently pouring the saline solution along the y-direction centre line of the sample, by slowly moving up and own along said centre line and pouring the saline with a speed of approximately 1 ml/sec. Then the caliper of the sample and the topsheet (20) and optionally core wrap at exactly the same points as before, but after wetting is determined as described above.

The average dry and wet calipers of the sublayer are calculated as follows:

Average Dry Caliper of the Sublayer=(average dry caliper of the sample comprising sublayer, topsheet, and optionally the core wrap)−(average dry caliper of the topsheet plus optionally core wrap).

Average Wet Caliper of the Sublayer=(average wet caliper of the sample comprising sublayer, topsheet, and optionally the core wrap)−(average wet caliper of the topsheet plus optionally core wrap).

The average caliper (34) loss after wetting (wet resilience) is then calculated as follows:

$$\frac{(\text{Av. Dry Caliper of the Sublayer}) - (\text{Av. Wet Caliper of the Sublayer})}{(\text{Av. dry caliper of the Sublayer})} \times 100\%$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for improved feces isolation and immobilization comprising a topsheet, a backsheet, an absorbent core positioned between the topsheet and the backsheet, and a sublayer positioned between the absorbent core and the topsheet and in contact with the topsheet,
   a) said topsheet comprising a liquid impermeable material and including an outermost body-faceable and body-contactable surface of the absorbent article and at least one topsheet region with a multitude of apertures configured to pass at least some feces, whereby
      i) the apertures have an average greatest aperture dimension in a cross-section in a plane of the body-faceable surface of the topsheet of from 2 mm to 8 mm when determined according to the test method for determining aperture and hole dimensions, the apertures each having a surface area in the cross-section; and
      ii) each topsheet region has a topsheet open area when measured according to the test method for determining open area and a topsheet surface area on the outermost body-faceable and body-contactable surface, said topsheet open area being from 20% to 55% of the topsheet surface area of said at least one topsheet region; and
   b) said sublayer comprising at least one acquisition layer and having a topsheet-facing surface and at least one sublayer region with a multitude of holes, whereby
      i) the holes have a z-direction caliper when measured according to the test method for determining caliper and an average smallest hole dimension from 3 mm to 10 mm when measured according to the test method for determining aperture and hole dimensions; and
      ii) each sublayer region in the topsheet-facing surface of the sublayer has a sublayer open area when measured according to the test method for determining open area and a sublayer surface area, said sublayer open area being from 20% to 50% of the sublayer surface area of said sublayer region;

wherein said average greatest dimension of the apertures is less than said average smallest dimension of the holes, and wherein at least one topsheet region is positioned above at least one sublayer region to form at least one overlap zone, the overlap zone having a surface area of at least 6 cm$^2$ and an overlap open area when measured according to the test method for determining open area, the apertures of the topsheet being positioned above, or partially above, holes of the sublayer in the overlap zone to form combined apertures, a cross-section of the combined apertures having a combined aperture surface area in a plane of the body-facing surface of the topsheet, the overlap open area being less than the topsheet open area and from 15% to 50% of the overlap zone surface area.

2. The absorbent article of claim 1, whereby said overlap open area is from 25% to 40% of the surface area of said overlap zone.

3. The absorbent article of claim 1, whereby the sublayer has an average caliper of at least 3 mm.

4. The absorbent article of claim 1, whereby the sublayer that forms part of the overlap zone has an average caliper loss after wetting of less than 20%, according to the Average Caliper Loss After Wetting method.

5. The absorbent article of claim 1, wherein said sublayer has holes that have a circular circumference with an average smallest dimension of from 4 mm to 10 mm, said holes being disposed in the topsheet-facing surface of the sublayer.

6. The absorbent article of claim 5, further comprising a front region, a back region and a crotch region therebetween, the overlap zone being present in only the back 70% of the absorbent article based on surface area.

7. The absorbent article of claim 1, whereby the sublayer comprises two or more acquisition layers and said holes are disposed in at least two of said acquisition layers, or a part thereof.

* * * * *

UNITED STATES PATENT AND TRADEMARK OFFICE
CERTIFICATE OF CORRECTION

| | | |
|---|---|---|
| PATENT NO. | : 7,956,236 B2 | |
| APPLICATION NO. | : 11/525606 | |
| DATED | : June 7, 2011 | |
| INVENTOR(S) | : Ponomarenko et al. | |

It is certified that error appears in the above-identified patent and that said Letters Patent is hereby corrected as shown below:

<u>On the Title Page</u>

Item (74)-Attorney, Agent or Firm, delete "Katheleen" and insert --Kathleen--.

<u>Column 5</u>

Line 32, delete "of the topsheet (20)".

Signed and Sealed this

Twentieth Day of March, 2012

David J. Kappos
*Director of the United States Patent and Trademark Office*